United States Patent [19]

Stevenson et al.

[11] 4,053,628
[45] Oct. 11, 1977

[54] COMPOSITION

[75] Inventors: Neil Arthur Stevenson; George Wardell, both of Loughborough, England

[73] Assignee: Fisons Limited, London, England

[21] Appl. No.: 677,274

[22] Filed: Apr. 15, 1976

Related U.S. Application Data

[60] Division of Ser. No. 471,141, May 17, 1974, Pat. No. 3,975,536, which is a continuation-in-part of Ser. No. 443,521, Feb. 19, 1974, abandoned, which is a continuation of Ser. No. 251,198, May 8, 1972, abandoned.

[30] Foreign Application Priority Data

| May 12, 1971 | United Kingdom | 14529/71 |
| Dec. 9, 1971 | United Kingdom | 57169/71 |
| May 25, 1973 | United Kingdom | 25237/73 |
| May 25, 1973 | United Kingdom | 25238/73 |
| June 5, 1973 | United Kingdom | 26649/73 |
| July 12, 1973 | United Kingdom | 33325/73 |

[51] Int. Cl.$^2$ .............................................. A61K 31/35
[52] U.S. Cl. .................................................. 424/283
[58] Field of Search ........................................ 424/283

[56] References Cited

U.S. PATENT DOCUMENTS

| 3,671,625 | 6/1972 | Altounyan | 424/83 |
| 3,686,412 | 8/1972 | Fitzmaurice et al. | 424/83 |
| 3,705,945 | 12/1972 | Fitzmaurice et al. | 424/83 |
| 3,720,690 | 3/1973 | King et al. | 424/83 |
| 3,777,033 | 12/1973 | Fitzmaurice et al. | 424/83 |
| 3,975,536 | 8/1976 | Stevenson et al. | 424/83 |

*Primary Examiner*—Donald B. Moyer
*Attorney, Agent, or Firm*—Wenderoth, Lind & Ponack

[57] ABSTRACT

There is described a composition comprising a substantially clear, sterile aqueous solution containing as active ingredient a therapeutically useful proportion of 1,3-bis(2-carboxy-chromon-5-yloxy)-propan-2-ol, or a pharmaceutically acceptable (e.g. the di-sodium) salt thereof, or of 5,5'-[[5,5'-(2-hydroxytrimethylene)dioxy]-bis[4-oxo-4H-1-benzopyran-2-yl]]tetrazole, or a pharmaceutically acceptable (e.g. the di-sodium) salt thereof. The composition is indicated for the treatment of conditions of the eye and the nose.

6 Claims, No Drawings

COMPOSITION

This application is a division of application Ser. No. 471,141, filed May 17, 1974 now U.S. Pat. No. 3,975,536, which application is in turn a continuation-in-part of application Ser. No. 443,521 filed Feb. 19, 1974 (now abandoned), which application is a continuation of application Ser. No. 251,198, filed May 8, 1972 (now abandoned).

This invention relates to new pharmaceutical compositions and methods for their preparation.

Initial attempts to formulate 1,3-bis(2-carboxychromon-5-yloxy)propan-2-ol, 5,5'-[[5,5'-(2-hydroxytrimethylene)dioxy]bis-[4-oxo-4H-1-benzopyran-2-yl]]tetrazole and their pharmaceutically acceptable salts as aqueous solutions produced compositions which rapidly became cloudy and were entirely unacceptable. A further difficulty was that the polar nature of the compounds and their high molecular weight indicated that they would combine with most of the known preservatives for aqueous pharmaceutical solutions to form insoluble precipitates thus simultaneously removing both active ingredient and preservative from the solution and further aggravating the problem of cloudiness mentioned above.

We have now found that it is possible to formulate these highly polar compounds in such a way that clear solutions are formed.

According to our invention we provide a composition comprising a substantially clear, sterile aqueous solution containing as active ingredient a therapeutically useful proportion of 1,3-bis(2-carboxy-chromon-5-yloxy)-propan-2-ol, or a pharmaceutically acceptable (e.g. the di-sodium) salt thereof, or of 5,5'-[[5,5'-(2-hydroxytrimethylene)dioxy]bis[4-oxo-4H-1-benzopyran-2-yl]]tetrazole, or a pharmaceutically acceptable (e.g. the di-sodium) salt thereof.

Parmaceutically acceptable salts include salts with alkali metal cations, e.g. sodium, potassium and lithium salts; ammonium salts and salts with organic bases, e.g. piperidine, triethanolamine or diethylaminoethylamine salts.

The solution may contain from 0.1 to 10%, preferably from 0.5 to 5% and more preferably about 1, 2 or 4% w/v of the active ingredient.

In addition to the active ingredient the composition may also contain an effective proportion of a pharmaceutically acceptable chelating or sequestering agent. Suitable sequestering or chelating agents include sodium charboxymethyl cellulose, citric, tartaric or phosphoric acid, and amino carboxylate compounds, preferably ethylenediamine tetraacetic acid or its salts, e.g. its calcium salt, its calcium-sodium salt, or more preferably its di-sodium salt. Further examples of amino carboxylate compounds are Perma Kleer 80 SO available from Refined Products Corporation of Lyndhurst N.J., USA and glycine derivatives, e.g. N,N-dihydroxy ethyl glycine and its salts, e.g. its sodium salt.

The concentration of the chelating or sequestering agent may vary considerably, but in any case should be such as to ensure that no precipitate of metal salts of the active ingredient occurs. A suitable concentration of chelating or sequestering agent may be from 0.005 to 0.1, and preferably from 0.01 to 0.1% w/v. When a very low concentration, i.e. less than about 0.40, preferably less than 0.32 ppm of 'metal ions' are present, for example when the solution contains less than 0.08 ppm of ionic iron and less than 0.25 ppm of ionic zinc, the chelating or sequestering agent may if desired by dispensed with. When a chelating or sequestering agent is used the concentration of 'metal ions' is preferably less than about 20 ppm and more preferably less than 10 ppm.

By the term 'metal ions' we mean ions of metals in groups IIa, Ib, IIb and IVb (also those of groups IIIa and IVa) of the periodic table and of the transition metals. Specific 'metal ions' which are detrimental, in excessive concentrations, i.e. above about 20 ppm, to the compositions of the invention are $Pb^{++}$ and $Ca^{++}$, (also $Cu^{++}$ and $Al^{+++}$) and in particular $Fe^{++}$, $Fe^{+++}$, $Zn^{++}$ and $Mg^{++}$ ions. We particularly prefer to keep the concentration of $Mg^{++}$ ions as low as possible, e.g. less than about 0.2 ppm and preferably less than about 0.12 ppm in the solution (less than about 2 ppm in the dry active ingredient and less than about 0.8 ppm in the water used to make the solution).

The composition may if desired contain an effective proportion, e.g. from 0.001 to 0.10% w/v, of a pharmaceutically acceptable preservative or sterilising agent. One example of a suitable preservative is sodium 2-(ethyl mercuriothio) benzoate known generically as "Thiomersal", which may be present in the composition in from 0.001 to 0.05 and preferably from 0.005 to 0.02, e.g. about 0.01% w/v. Other suitable preservatives include pharmaceutically acceptable quaternary ammonium compounds, e.g. cetyl pyridinium chloride, tetradecyltrimethyl ammonium bromide known generically as 'Centrimide', benzyl dimethyl [2-[2-[p-(1,1,3,3-tetramethyl butyl)]phenoxy]ethoxy] ammonium chloride, known generically as 'Benzethonium chloride', and myristyl-γ-picolinium chloride, anyone of which may be used at a concentration of from about 0.002 to 0.05, e.g. about 0.02% w/v. The preferred preservatives amongst the quaternary ammonium compounds are however the alkyl benzyl dimethyl ammonium chlorides and mixtures thereof, e.g. that known generically as 'Benzalkonium chloride'. This latter consists of a mixture of compounds of formula

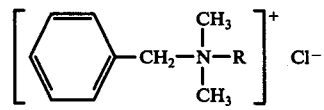

in which R is an alkyl group $C_8H_{17}$ to $C_{18}H_{37}$. We particularly prefer to use a mixture of such compounds in which R is $C_{10}H_{21}$ to $C_{14}H_{29}$ and especially that specific compound in which R is $C_{12}H_{25}$. 'Benzalkonium chloride', and the compounds of the formula given above, may be used at a concentration of from 0.005 to 0.10 preferably 0.005 to 0.05, e.g. about 0.01% w/v and may optionally be used in combination with 0.2 to 2.0, e.g. 0.4% w/v of 2-phenylethanol (BPC 1963). 'Benzalkonium chloride' (and the compounds of the formula given above) and 2-phenylethanol have been found to have a synergistic effect, particularly against *Pseudomonas aeruginosa*, when used in combination with the di-sodium salt of ethylenediamine tetra acetic acid.

The composition may also contain conventional excipients, e.g. sodium chloride, dextrose or mannitel, and buffers, e.g. sodium dihydrogen orthophosphate (sodium acid phosphate BP), di-sodium hydrogen phosphate (sodium phosphate BP) sodium citrate/citric acid, and boric acid/sodium borate. The proportion and concentration of excipients and buffers may be varied within fairly wide ranges, provided the resulting solution is stable and non-irritant when applied to the appropriate tissues. For maximum stability the preferred pH is from 4 to 7.5, preferably 4 to 7.0, with minimal buffering to avoid tissue irritation. The maximum total concentration of excipients and buffers is preferably less than 5% w/v and more preferably less than 2% w/v.

The composition may also contain one or more additional compounds which are therapeutically useful in the eye.

Examples of such additional therapeutically useful compounds include other anti-allergic agents, e.g. anti-histamines and anti-inflammatory agents; decongestants; anti-viral agents and vasoconstrictors.

As anti-histamine compounds there may be mentioned, for example Antazoline or diphenhydramine hydrochloride.

As anti-inflammatory agents there may be mentioned anti-inflammatory steroids, for example Prednisolone; anti-bacterials, for example sulphacetamide and propamidine isethionate; antibiotics, for example Tetracycline, Chloramphenicol, Neomycin or Framycetin and anti-micotic agents, for example nystatin or amphotericin B.

As an example of decongestants there may be mentioned Phenylephrine.

As an example of anti-viral agents there may be mentioned Idoxuridine.

As an example of vasoconstrictors there may be mentioned Oxymetazoline.

The additional therapeutically useful compounds should, of course, be present in a therapeutically useful proportion. In general the additional compoinds, other than the anti-biotics, may be present at a concentration of from about 0.05 to 0.6% w/v. The anti-bacterials may however in certain cases by present in greater concentrations, for example up to 10, 20 or even 30% w/v.

We also provide a method of treatment of conditions of the eye which comprises the use of the additional therapeutically useful compounds separately from, but simultaneously with the compositions described herein which do not contain the additional therapeutically useful compound, i.e. concurrent therapy rather than therapy with a mixture.

Examples of suitable concentrations (w/v) of additional therapeutically useful compounds in the compositions of this invention are given below:

| | |
|---|---|
| Idoxuridine | 0.1% |
| Oxymetazoline | 0.05% |
| Phenylephrine HCl (eye drops) | 0.10% |
| Antazoline phosphate | 0.5% |
| Diphenhydramine hydrochloride | 0.2% |
| Prednisolone sodium phosphate | 0.518% |
| Chloramphenicol | 0.5% |
| Sulphacetamide sodium | 10–30% |
| Tetracycline | 1–3% |
| Nystatin | 1% |

The composition may also contain additives designed to increase the viscosity and/or to prolong the action of the active ingredient.

Suitable additives include cellulosic compounds, e.g. methyl cellulose, hydroxypropylmethyl cellulose, hydroxypropylethyl cellulose, hydroxyethyl cellulose and ethylhydroxyethyl cellulose; polyvinyl alcohols; gelatin; polyvinylpyrolidone; polyethylene glycols; propylene glycol and glycerin.

Combinations of additives may be used if desired.

The concentration of the additives in the solution may be in the range 0.25 to 5% w/v and is preferably in the range 0.5 to 1.5% w/v.

The additives may of course be present in addition to any chelelating or sequestering agents, preservatives, excipients, buffers, additional therapeutically useful compounds etc.

The composition, when it does not contain a preservative, may be made up using conventional techniques, e.g. by dissolving the chelating or sequestering agent (if included) in freshly distilled water, adding the excipients, buffers etc to the aqueous solution of chelating or sequestering agent, adding the active ingredient to the resulting solution, stirring, filtering and then sterilising the composition by autoclaving, for example at a temperature of about 115° C for about 30 minutes. The autoclaving of the product may, if desired, be omitted when the composition is produced by sterile filtration into a previously sterilised container under aseptic conditions.

Compositions which contain preservatives may be made up by mixing two aqueous solutions of equal volumes one containing twice the desired final concentration of the active ingredient, chelating or sequestering agent, and other additives, and the other containing twice the desired final concentration of the preservative. The resulting mixture may then be filtered under sterile conditions. Surprisingly we find that mixture of a solution of the anionic active ingredient with a solution of a cationic quaternary ammonium preservative does not precipitate all the preservative from the mixed solution.

The components of the composition should be as free as possible from 'metal ions' and contact with materials yielding such ions should be avoided during manufacture. If desired 'metal ions' may be removed from the components of the composition by conventional means, e.g. by ion exchange.

According to the invention there is also provided a method of treatment of conditions of the eye or nose, in which conditions allergy or immune reactions play a contributory part, which method comprises administration of a composition according to the invention or some other form of 1,3-bis(2-carboxychromon-5-yloxy) propan-2-ol, or a pharmaceutically acceptabtable salt, e.g. the di-sodium salt, ester, e.g. a C 1 to 6 alkyl ester, or amide (e.g. the amide derived from ammonia) thereof topically or by sub-conjunctival injection to a patient having such a condition.

The dosage to be administered will of course vary with the condition to be treated, with its severity and with its location. However, in general for use in the eye a dosage of about 1 or 2 drops (e.g. from 0.66 to 1.32 mg of active ingredient) into the affected eye from 2 to 4 times a day is found to be satisfactory. More frequent dosage may, of course, be used if desired. For use in the nose a dosage of about 0.16 ml (e.g. about 3.2 mg of active ingredient) is indicated (0.08 ml per nostril).

Conditions of the outer eye in which the method of the invention has proved successful include vernal catarrh (vernal kerato-conjunctivitis) and marginal corneal ulceration or infiltration. Other conditions which may be treated by the method of the invention include the occular effects of hay fever, 'allergic eyes' where the allergen is known or unknown and spring/summer conjunctivitis. This latter term is used to mean allergic disorders of the eyes occurring in the spring and summer where an external allergen plays a part in the disorder. Further conditions of the eye which may be mentioned are 'irritable eye' or 'non-specific conjunctivitis', Herpes Simplex Keratitis and Conjunctivitis, Herpes Zoster Keratitis and Conjunctivitis, adenovirus infections, phlyctenular conjunctivitis, corneal homograft rejection, Trachoma, anterior uveitis and drug sensitivity.

Conditions of the nose which may be mentioned include seasonal rhinitis, e.g. hay fever; perennial rhinitis, nasal polyps and allergic manifestations of the nasopharynx. Preserved solutions are particularly useful in the treatment of conditions of the nose, e.g. as a nasal spray containing 2% of active ingredient.

The unpreserved compositions may be put up in single applications containers containing from 0.3 to 0.7 ml of solution and the preserved compositions may be put up in multi-dose (plastics, e.g. polyethylene, or glass) packs containing 5 to 20, preferably 7.5 or 17.5 ml of solution.

We also provide solutions suitable for injection, e.g. sub-conjunctivally, preferably sterile unpreserved solutions which are substantially free of particulate material.

Whether a solution is substantially clear will be readily determinable by those skilled in the art, and will depend on the number, size and type of particles in the solution. Thus large particles are less acceptable than are particles of less than 50 microns in diameter. We prefer the solutions of the invention to contain less than 20, preferably less than 16 and more preferably less than 12 particles per 8 mls of solution when the solution is viewed in a particle free container under the magnifyer of a polarised light viewer. Desirably the solution contains less than 4 such particles per 8 mls.

The invention is illustrated but in no way limited by the following Examples:

EXAMPLE 1

| Unpreserved eye drop solution | |
|---|---|
| Di-sodium salt of 1,3-bis(2-carboxy-chromon-5-yloxy)-propan-2-ol | 1.0% w/v |
| Sodium chloride BP | 0.56% w/v |
| Sodium acid phosphate BP | 0.26% w/v |
| Sodium phosphate BP | 0.59% w/v |
| Di-sodium edetate BP | 0.01% w/v |
| Distilled water | to 100% |

EXAMPLE 2

| Preserved Nasal Spray Solution | |
|---|---|
| Di-sodium salt of 1,3-bis(2-carboxy-chromon-5-yloxy)-propan-2-ol (Sodium cromoglycate BP) | 2.0% w/v |
| Di-sodium edetate BP | 0.01% w/v |
| Thiomersal BP | 0.01% w/v |
| Sterile distilled water | to 100% |

Thiomersal BP may be replaced by the following preservatives

| Benzalkonium chloride USP | 0.01% w/v |
|---|---|
| Benzalkonium chloride solution BP | 0.02% w/v |
| Benzethonium chloride | 0.02% w/v |
| Centrimide BP | 0.02% w/v |
| Myristyl-γ-picolinium chloride | 0.02% w/v |
| Chlorocresol BP | 0.1% w/v |
| Chlorbutol BP | 0.5% w/v |
| Chlorhexidine salts (e.g. acetate, glyconate) | 0.005–0.01% w/v |
| Phenyl mercuric salts (e.g. nitrate, acetate) | 0.1% w/v |
| p-hydroxy benzoates | 0.4–0.8% w/v |
| Phenylethyl alcohol BPC 1963 | 0.3–0.6% w/v |
| Cetyl pyridinium chloride BP | 0.02% w/v |
| Domiphen bromide BP | 0.01% w/v |
| or Phenoxyethanol BPC | 0.5–1.0% w/v |

Pharmaceutically acceptable combinations of the above preservatives may also be used

| e.g. Benzalkonium chloride BP | 0.02% w/v |
|---|---|
| + Phenylethylalcohol | 0.4% w/v |
| p-hydroxybenzoates | |
| + phenoxyethanol BPC | } 0.4% ('Phenonip') |

The sodium cromoglycate BP may be replaced by

| 5,5'-[[5,5'-(2-hydroxytrimethylene)-dioxy]bis[4-oxo-4H-1-benzopyran-2-yl]]tetrazole di-sodium salt | 2.0% w/v |
|---|---|

EXAMPLE 3

| Preserved Buffered isotonic eye-drop solution | |
|---|---|
| Sodium cromoglycate BP | 1.0% w/v |
| Di-sodium edetate BP | 0.01% w/v |
| Sodium chloride BP | 0.42% w/v |
| Sodium phosphate BP ($Na_2HPO_4 \cdot 12H_2O$) | 0.12% w/v |
| Sodium acid phosphate BP ($NaH_2PO_4 \cdot 2H_2O$) | 0.47% w/v |
| Thiomersal BP | 0.01% w/v |
| Sterile distilled water | |

Thiomersal BP may be replaced by any of the preservatives listed in Example 2. In some cases, the quantity of sodium chloride in the formulation may have to be adjusted to maintain isotonicity.

EXAMPLE 4

| Sodium cromoglycate BP | 2.0% w/v |
|---|---|
| Disodium edetate BP | 0.01% w/v |
| Thiomersal BP | 0.002% w/v |
| Sterile distilled water | to 100% w/v |

200g of sodium cromoglycate, 1g of sodium edetate and 0.20g of Thiomersal are dissolved with stirring in 10 litres of sterile distilled water. The resulting solution is then sterile filtered and bottled in 10 or 15 ml bottles.

EXAMPLE 5

| Sodium cromoglycate BP | 2.0% w/v |
|---|---|
| Disodium edetate BP | 0.01% w/v |
| Benzalkonium chloride solution BP | 0.04% w/v |
| Phenylethyl alcohol BPC 1963 | 0.4% w/v |
| Sterile distilled water | to 100% w/v |

1g of sodium edetate and 200g of sodium cromoglycate are dissolved, in that order, with stirring in 4 litres of sterile filtered distilled water to yield a solution A. 40g of phenylethyl alcohol and 4 ml of Benzalkonium chloride are dissolved, in that order, in 4 litres of sterile filtered distilled water with gentle stirring to yield a solution B. Solution B is then added gradually over a period of 5 minutes to solution A with stirring. The resulting solution is then made up to 10 litres with sterile filtered distilled water, stirred for 20 minutes, allowed to settle and filtered under pressure through a Whatman gamma 12 filter. The filtered solution is then bottled in 10 or 15 ml bottles.

EXAMPLE 6

| Composition designed to increase the viscosity of solution | |
| --- | --- |
| Sodium cromoglycate BP | 2.0% w/v |
| Di-sodium edetate BP | 0.01% w/v |
| Benzalkonium chloride solution BP | 0.04% v/v |
| Phenylethyl alcohol BPC 1963 | 0.4% w/v |
| Sodium carboxymethyl cellulose 'Edifas' B50 | 0.5% w/v |
| Sterile distilled water | to 100% w/v |

We claim:

1. A method of treatment of conditions of the eye or nose, in which conditions allergy or immune reactions play a contributory part, which method comprises administration of 1,3-bis(2-carboxychromon-5-yloxy)propan-2-ol, or a pharmaceutically acceptable salt thereof, topically or by sub-conjunctival injection to a patient having such a condition.

2. A method for the treatment of conditions of the eye or nose in which conditions allergy or immune reactions play a contributory part which comprises administering topically or by sub-conjunctival injection to a patient suffering from such condition a composition which comprises a sterile aqueous solution containing 1,3-bis(2-carboxy-chromon-5-yloxy)-propan-2-ol or a pharmaceutically acceptable salt thereof as an active ingredient, wherein, in said composition, the said active ingredient is present in an amount of from 0.1 to 10% w/v, the said composition containes less than about 0.40 ppm of ions of metals in Groups IIa, Ib, IIb and IVb of the Periodic Table and of the transition metals, the said composition being a substantially clear, sterile aqueous solution.

3. A method for the treatment of conditions of the eye or nose in which conditions allergy or immune reactions play a contributory part which comprises administering topically or by sub-conjunctival injection to a patient suffering from such condition a compostion which comprises a sterile aqueous solution containing 1,3-bis(2-carboxy-chromon-5-yloxy)-propan-2-ol or a pharmaceutically acceptable salt thereof as an active ingredient, wherein, in said composition, the said active ingredient is present in an amount of from 0.1 to 10% w/v, the composition contains less than about 20ppm of ions of metals in Groups IIa, Ib, IIb and IVb of the Periodic Table and of the transition metals, the composition contains from about 0.05 to 0.1% w/v of a pharmaceutically acceptable chelating or sequestering agent, and the said composition is a substantially clear aqueous solution.

4. A method according to claim 1 wherein the condition to be treated is a condition of the eye selected from the group of vernal catarrh, marginal corneal ulceration or infiltration, occular effects of hay fever, non-specific conjunctivitis, Herpes Simplex Keratitis and Conjunctivitis, Herpes Zoster Keratitis and Conjunctivitis, adenovirus infections, phlyctenular conjunctivitis, corneal homograft rejection, Trachoma, anterior uveitis and drug sensitivity.

5. A method according to claim 1 wherein the condition to be treated is a condition of the nose selected from the group of seasonal rhinitis, perennial rhinitis, nasal polyps and allergic manifestations of the nasopharynx.

6. A method according to claim 4 wherein the dosage to be administered is from 0.66 to 1.32 mg. of the 1,3-bis(2-carboxychromon-5-yloxy)propan-2-ol or pharmaceutically acceptable salt thereof to the affected eye from 2 to 4 times per day.

* * * * *